United States Patent [19]
Birrenbach et al.

[11] Patent Number: 5,897,877
[45] Date of Patent: Apr. 27, 1999

[54] ORAL PHARMACEUTICAL PREPARATION CONTAINING ERYTHROMYCIN BASE

[75] Inventors: Gerd Birrenbach, Kappel; Rolf Dieter Juch, Wangen B. Olten, both of Switzerland

[73] Assignee: Spirig AG, Pharmazeutische Praeparate, Egerkingen, Switzerland

[21] Appl. No.: 08/495,968

[22] Filed: Jun. 28, 1995

[30] Foreign Application Priority Data

Jun. 28, 1994 [CH] Switzerland .......................... 2-048/94

[51] Int. Cl.⁶ ........................................................ A61K 9/20
[52] U.S. Cl. .............................. 424/465; 424/471; 514/29
[58] Field of Search ...................................... 424/464, 465, 424/468, 469, 471, 472–482; 574/29

[56] References Cited

U.S. PATENT DOCUMENTS 5,049,394  9/1991  Howard et al. ......................... 424/490
5,225,202  7/1993  Hodges et al. ......................... 424/480

FOREIGN PATENT DOCUMENTS 207041      12/1986   European Pat. Off. .
2204241     11/1988   United Kingdom .
WO 94/03160  2/1994   WIPO .

OTHER PUBLICATIONS

Charman et al: J. Bone JT. SURG. Serv.A. 1976 5811 (76–B1) Effect of Polymethacrylate & Antibiotic Combinations.

Primary Examiner—Neil S. Levy
Attorney, Agent, or Firm—Lahive & Cockfield, LLP

[57] ABSTRACT

Basic pellets containing erythromycin base, to which a small amount of a slightly acid salt, such as potassium dihydrogen phosphate and possibly an additive is added for improved release of the active substance in the intestinal tract, are provided with a coating that contains a polymer resistant to gastric juice, such as poly(methacrylic acid, -ethylacrylate), a separating agent, such as talc, and a softening agent, such as diethyl phthalate.

21 Claims, 1 Drawing Sheet

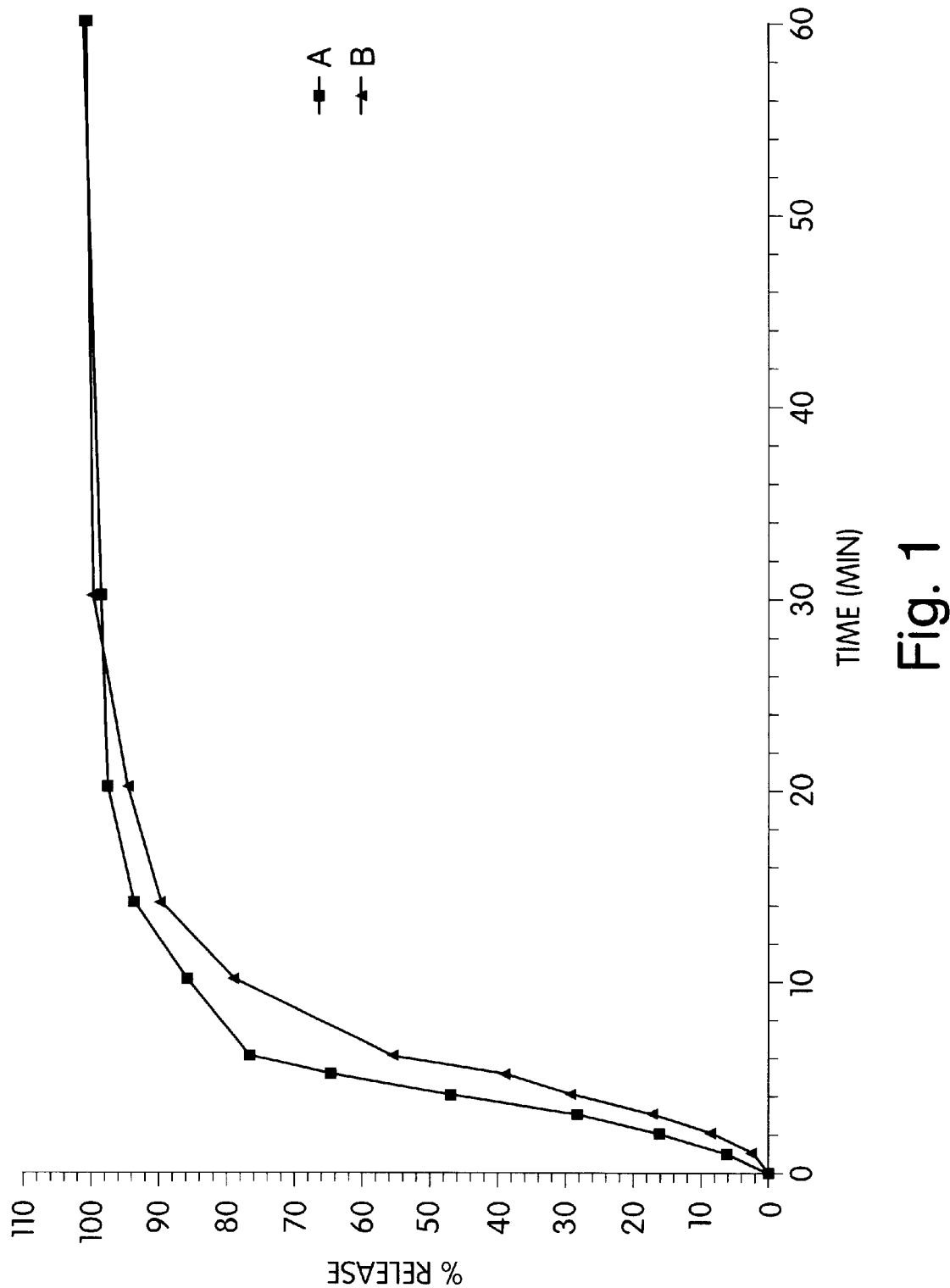

ORAL PHARMACEUTICAL PREPARATION CONTAINING ERYTHROMYCIN BASE

Priority under 35USC119(e) is claimed to Swiss 02 048/94-7 filed Jun. 8, 1998.

The invention relates to a novel oral pharmaceutical preparation containing erythromycin, as described in claim 1.

BACKGROUND OF THE INVENTION

The macrolide antibiotic erythromycin has been used successfully for a long time as a pharmaceutical preparation with bacteriostatic or bactericidal action. It is usually used in the form of esters, for example as ethyl succinate, stearate, estolate, glucoheptonate, or lactobionate, which considerably increases the volume of the finished pharmaceutical preparation because of the ester residue.

On the other hand, because the erythromycin base dissolves readily in an acid medium but only with difficulty in a basic medium, it is difficult to achieve rapid release of the active substance in the basic intestinal tract without adding large quantities of additives. By adding approximately 4–10 wt. %, based on an uncoated basic pellet, of compounds that are readily soluble in water, such as PEG, saccharose, nicotinamide, or adenosine triphosphate, rapid release of the active substance, for example in phosphate buffer with pH 7.4, could not be achieved.

On the other hand, however, the erythromycin base must be protected by an enteric coating during its passage through the stomach, because it disintegrates at a pH of <4.0. Because enteric-coated preparations, for example tablets with a diameter of more than 8 mm, have been shown to remain for a long time in the stomach without disintegrating, the erythromycin base must advantageously be formulated as pellets for rapid passage through the stomach.

The aqueous preparation of erythromycin base to form pellets however entails complications because the active substance exhibits pronounced lipophilic properties and is therefore difficult to wet with water.

SUMMARY OF THE INVENTION

The goal of the invention is to develop a formulation containing erythromycin base with a high active substance content of >80 wt. %, preferably >90 wt. %, based on the uncoated pellet weight, which quickly releases the active substance in the intestinal tract.

Another goal of the invention consists in switching the manufacturing process to avoid organic solvents in the product and in the environment, to the exclusive use of water.

This goal is achieved by the features defined in the characterizing clause of the claims.

BRIEF DESCRIPTION OF THE FIGURES

FIG. 1 shows the in vitro release of erythromycin from two erythromycin-based pellets, manufactured according to Example 1, which were sprayed with a coating prepared according to Example 5. Pellet A was sprayed in two steps staggered timewise with respect to one another. Pellet B was sprayed in a single work step. In vitro release of the erythromycin base was measured according to USP XXII, phosphate buffer pH 7.4 following a previous 2-hour pretreatment in synthetic gastric juice according to Ph.H. VI.

DETAILED DESCRIPTION OF THE INVENTION

Surprisingly, it has been found that the use of small quantities of slightly acid salts having a $pK_a$ ranging from, for example, 3 to 6.5, and which are toxicologically and physiologically acceptable considerably increases the release of the erythromycin base in a phosphate buffer with pH 7.4. Thus, for example, by adding approximately 1–15 wt. %, based on the uncoated pellet weight, preferably 3–8 wt. %, especially preferably approximately 4 wt. %, $KH_2PO_4$ for pellet formulation, dissolution of the pellets within 15 minutes is ensured.

Other suitable slightly acid salts for example include potassium dihydrogen citrate, potassium hydrogen tartrate, potassium hydrogen phthalate, potassium dihydrogen phosphate, sodium dihydrogen phosphate, or disodium hydrogen citrate, which can be used individually or as a mixture.

In order to increase the strength of the pellets, additives, for example lactose, kaolin, dicalcium phosphate, maltose, corn starch, or preferably microcrystalline cellulose in a quantity of 0–20 wt. %, preferably 3–9 wt. %, especially preferably approximately 6 wt. %, may be added.

The pellets according to the invention are produced with the aid of a rotary method, preferably in a rotary processor (for example Niro-Aeromatic, Bubendorf, Switzerland), by spraying the active ingredient and possibly the additive mixture with the salt solution and possibly with water, but if desired other conventional devices may be used, for example the Diosna mixer (for example Dierks u. Söhne, Osnabrück, Germany), with adaptation of the process parameters.

In this manner, pellets with high density and rapid dissolution in phosphate buffer with pH 7.4 are obtained. An enteric coating is sprayed onto these pellets, said coating containing at least one polymer resistant to gastric juice, at least one separating agent, and at least one softening agent.

The polymer resistant to gastric juice is applied in a quantity of 5–40 wt. %, based on the weight of the basic pellets without the coating, preferably 15–30 wt. %, especially preferably approximately 24 wt. %, the separating agent in a quantity of 1–15 wt. %, preferably 2–10 wt. %, especially preferably approximately 3.75 wt. %, and the softening agent in an amount of 1–20 wt. %, preferably 2–10 wt. %, especially preferably 2.4 wt. % onto the basic pellet.

Suitable polymers resistant to gastric juice include in particular poly(methacrylic acid, -ethylacrylate), for example Eudragit L30D, or polyvinyl acetate phthalate, cellulose acetate phthalate, hydroxypropylmethylcellulose acetate succinate, or carboxymethylethylcellulose alone or mixed with one another.

Suitable separating agents include for example magnesium stearate, hydrogenated castor oil, dipropyl glycol dipelargonate, glycerin monobehenate, and especially talc, alone or mixed with one another.

Suitable softening agents include for example polyethylene glycol, distilled acetylated monoglycerides, triethyl citrate, glycerin triacetate, acetyltriethyl citrate, or preferably diethyl phthalate alone, or mixed with one another.

The pellets according to the invention are preferably sprayed and then dried in a fluidized bed granulator with an aqueous dispersion, consisting of a mixture of a polymer resistant to gastric juice, a separating agents, and a softening agent.

The pellets are suitable for filling hard gelatin capsules. The small additive requirement and the considerable compaction of the pellets gives them a bulk volume of about 130–160 ml/100 g. This makes possible pellets corresponding to a dose of 300 mg erythromycin base in a size 0 gelatin capsule, while usually a dose of only 250 mg/capsule is conventional.

The invention is described in greater detail in the following examples.

EXAMPLE 1

Basic pellets with the following composition were prepared:

| | |
|---|---|
| Erythromycin base | 90.0 g |
| Potassium dihydrogen phosphate | 4.0 g |
| Microcrystalline cellulose | 6.0 g |

The active substance and additives were loaded into the rotary processor. The slightly acid salt was dissolved in purified water. Then the mixture of active substance and additives was sprayed with the salt solution and then with purified water as necessary until pellets of the desired size had formed. The pellets were then dried by raising the inner cylinder in the process airstream.

EXAMPLE 2

Basic pellets with the following composition were prepared:

| | |
|---|---|
| Erythromycin base | 82.0 g |
| Potassium hydrogen phthalate | 8.0 g |
| Lactose | 10.0 g |

The basic pellets were prepared as described in Example 1.

EXAMPLE 3

Basic pellets with the following composition were prepared:

| | |
|---|---|
| Erythromycin base | 84.0 g |
| Disodium hydrogen citrate | 6.0 g |
| Corn starch | 10.0 g |

The basic pellets were prepared as described in Example 1.

EXAMPLE 4

Basic pellets with the following composition were prepared:

| | |
|---|---|
| Erythromycin base | 80.0 g |
| Potassium hydrogen tartrate | 8.0 g |
| Kaolin | 6.0 g |
| Dicalcium phosphate | 6.0 g |

The basic pellets were prepared as described in Example 1.

EXAMPLE 5

A coating with the following composition was sprayed onto the basic pellets of Examples 1–4 (the amounts were calculated on the basis of the weight of the basic pellets):

| | |
|---|---|
| Poly(methacrylic acid, -ethylacrylate) | 23.85% |
| Diethyl phthalate | 2.40% |
| Talc | 3.75% |

An aqueous dispersion was prepared composed of gastric juice-resistant polymer, the separating agent, and the softening agent. The basic pellets prepared in accordance with one of Examples 1–4 were then sprayed in a fluidized bed granulator with this dispersion. After the spray application, the coated pellets were dried.

EXAMPLE 6

A coating with the following composition was sprayed onto the basic pellets of Examples 1–4 (the amounts were calculated on the basis of the weight of the basic pellets):

| | |
|---|---|
| Cellulose acetate phthalate | 20.0% |
| Acetyltriethyl citrate | 4.8% |
| Magnesium stearate | 2.2% |

The basic pellets were sprayed with the coating as described in Example 5 and dried.

EXAMPLE 7

A coating with the following composition was sprayed onto the basic pellets of Examples 1–4 (the amounts were calculated on the basis of the weight of the basic pellets):

| | |
|---|---|
| Hydroxypropylmethylcellulose acetate succinate | 20.0% |
| Triethyl citrate | 6.0% |
| Talc | 6.0% |

The basic pellets were sprayed with the coating as described in Example 5 and dried.

EXAMPLE 8

A coating with the following composition was sprayed onto the basic pellets of Examples 1–4 (the amounts were calculated on the basis of the weight of the basic pellets):

| | |
|---|---|
| Carboxymethylethylcellulose | 20.0% |
| Distilled acetylated monoglycerides | 6.0% |
| Hydrogenated castor oil | 6.0% |

The basic pellets were sprayed with the coating as described in Example 5 and dried.

EXAMPLE 9

Basic pellets manufactured according to Example 1 were sprayed in two experiments, A and B, with a coating prepared according to Example 5. The difference between experiments A and B consists in the fact that the coating in experiment A was sprayed on in two work steps staggered timewise with respect to one another and in experiment B in a single work step. After drying, the in vitro release of the erythromycin base was measured according to USP XXII, phosphate buffer pH 7.4 following a previous 2-hour pretreatment in synthetic gastric juice according to Ph.H. VI. The results are shown in FIG. 1.

We claim:

1. A pharmaceutical preparation, in pellet form, having a core comprising erythromycin and at least one acidic salt, wherein said erythromycin constitutes greater than 80% by weight of said core, and wherein said core is coated with an enteric coating.

2. The pharmaceutical preparation according to claim 1 further comprising at least one additive.

3. The pharmaceutical preparation according to claim 1, wherein the erythromycin is present in an amount of at least 90% by weight, based on the core weight.

4. The pharmaceutical preparation according to claim 1, wherein the acidic salt constitutes approximately 1–15% by weight of said core.

5. The pharmaceutical preparation according to claim 4, wherein the acidic salt constitutes 3–8% by weight of said core.

6. The pharmaceutical preparation according to claim 5, wherein the acidic salt constitutes 4% by weight of said core.

7. The pharmaceutical preparation according to claim 1, wherein the acidic salt is selected from the group consisting of potassium dihydrogen citrate, potassium hydrogen tartrate, potassium hydrogen phthalate, sodium dihydrogen phosphate, and disodium hydrogen citrate, potassium dihydrogen phosphate, and a combination thereof.

8. The pharmaceutical preparation according to claim 7, wherein the acidic salt comprises potassium dihydrogen phosphate.

9. The pharmaceutical preparation according to claim 2, wherein the additive is microcrystalline cellulose.

10. The pharmaceutical preparation according to claim 2, wherein the additive constitutes 3–9% by weight of said core.

11. The pharmaceutical preparation according to claim 2, wherein the additive constitutes 6% by weight of said core.

12. The pharmaceutical preparation according to claim 1, wherein the enteric coating comprises a polymer resistant to gastric juice, at least one separating agent, and at least one softening agent.

13. The pharmaceutical preparation according to claim 12, wherein the enteric coating constitutes 5–40% by weight of said core, wherein the polymer resistant to gastric juice constitutes 1–15% by weight of said core, and wherein the separating agent constitutes 1–20% by weight of said core.

14. The pharmaceutical preparation according to claim 13, wherein the enteric coating constitutes 15–30% by weight of said core, wherein the polymer resistant to gastric juice constitutes 2–10 % by weight of said core, and wherein the separating agent constitutes 2–10% by weight of said core.

15. The pharmaceutical preparation according to claim 14, wherein the enteric coating constitutes 24% by weight of said core, wherein the polymer resistant to gastric juice constitutes 3.75 % by weight of said core, and wherein the separating agent constitutes 2.4% by weight of said core.

16. The pharmaceutical preparation according to claim 13, wherein the polymer resistant to gastric juice comprises a polymer selected from the group consisting of polyvinyl acetate phthalate, cellulose acetate phthalate, hydroxypropylmethylcellulose acetate succinate, carboxymethylethylcellulose, poly(methacrylic acid, -ethylacrylate), and a combination thereof.

17. The pharmaceutical preparation according to claim 16, wherein the polymer resistant to gastric juice comprises poly(methacrylic acid, -ethylacrylate).

18. The pharmaceutical preparation according to claim 12, wherein the separating agent comprises an agent selected from the group consisting of magnesium stearate, hydrogenated castor oil, dipropyl glycol dipelargonate, glycerin monobehenate talc, and a combination thereof.

19. The pharmaceutical preparation according to claim 18, wherein the separating agent comprises talc.

20. The pharmaceutical preparation according to claim 12, wherein the softening agent comprises an agent selected from the group consisting of polyethylene glycol, distilled acetylated monoglycerides, triethyl citrate, glycerin triacetate, acetyltriethyl citrate, and diethyl phthalate, and a combination thereof.

21. The pharmaceutical preparation according to claim 20, wherein the softening agent comprises diethyl phthalate.

* * * * *